(12) United States Patent
Suplie et al.

(10) Patent No.: US 8,999,392 B2
(45) Date of Patent: Apr. 7, 2015

(54) PHARMACEUTICAL FORMULATIONS TO PREVENT THE MISUSE OF MEDICINAL DRUGS

(75) Inventors: Pascal Suplie, Montaure (FR); Christophe Lebon, Rouvres (FR)

(73) Assignee: Debregeas et Associes Pharma, Paris (FR)

( * ) Notice: Subject to any disclaimer, the term of this patent is extended or adjusted under 35 U.S.C. 154(b) by 0 days.

(21) Appl. No.: 13/390,213

(22) PCT Filed: Aug. 11, 2010

(86) PCT No.: PCT/FR2010/051697
§ 371 (c)(1), (2), (4) Date: Mar. 9, 2012

(87) PCT Pub. No.: WO2011/018583
PCT Pub. Date: Feb. 17, 2011

(65) Prior Publication Data
US 2012/0164228 A1 Jun. 28, 2012

(30) Foreign Application Priority Data
Aug. 12, 2009 (FR) ..................................... 09 55642

(51) Int. Cl.
| | | |
|---|---|---|
| A61K 9/16 | (2006.01) | |
| A61K 31/485 | (2006.01) | |
| A61K 31/352 | (2006.01) | |
| A61K 31/5513 | (2006.01) | |
| A61K 31/135 | (2006.01) | |
| A61K 31/197 | (2006.01) | |
| A61K 33/08 | (2006.01) | |
| A61K 33/06 | (2006.01) | |
| A61K 47/38 | (2006.01) | |
| A61K 47/36 | (2006.01) | |
| A61K 8/60 | (2006.01) | |
| A61K 9/46 | (2006.01) | |
| A61K 9/48 | (2006.01) | |
| A61K 9/20 | (2006.01) | |
| A61K 33/10 | (2006.01) | |
| A61K 8/73 | (2006.01) | |
| A61K 8/23 | (2006.01) | |
| A61K 31/27 | (2006.01) | |
| A61K 8/41 | (2006.01) | |
| A61K 8/97 | (2006.01) | |
| A61K 51/04 | (2006.01) | |
| A61K 8/29 | (2006.01) | |

(52) U.S. Cl.
CPC ............ *A61K 9/4858* (2013.01); *A61K 9/1694* (2013.01); *A61K 31/485* (2013.01); *A61K 31/352* (2013.01); *A61K 31/5513* (2013.01); *A61K 9/1611* (2013.01); *A61K 9/1676* (2013.01); *A61K 31/135* (2013.01); *A61K 31/197* (2013.01); *A61K 33/10* (2013.01); *A61K 2800/43* (2013.01); *A61K 8/732* (2013.01); *A61K 9/0007* (2013.01); *A61K 8/23* (2013.01); *A61K 31/27* (2013.01); *A61K 8/41* (2013.01); *A61K 8/97* (2013.01); *A61K 51/0489* (2013.01); *A61K 33/08* (2013.01); *A61K 2800/22* (2013.01); *A61K 8/29* (2013.01); *A61K 9/1623* (2013.01); *A61K 9/1652* (2013.01); *A61K 9/2009* (2013.01); *A61K 9/2013* (2013.01); *A61K 9/2018* (2013.01); *A61K 9/2054* (2013.01); *A61K 9/2077* (2013.01); *A61K 9/4866* (2013.01)

(58) Field of Classification Search
CPC . A61K 9/1623; A61K 9/1652; A61K 9/2009; A61K 9/2013; A61K 9/2018; A61K 9/2054; A61K 9/2077; A61K 9/4858; A61K 9/4866
See application file for complete search history.

(56) References Cited

U.S. PATENT DOCUMENTS

| | | | |
|---|---|---|---|
| 4,101,650 A | 7/1978 | Umezawa | |
| 4,424,235 A | 1/1984 | Sheth et al. | |
| 5,824,339 A * | 10/1998 | Shimizu et al. | ............... 424/466 |
| 5,846,971 A * | 12/1998 | Sangekar et al. | ........ 514/254.07 |
| 6,214,386 B1 | 4/2001 | Santus et al. | |
| 6,264,989 B1 | 7/2001 | Kato et al. | |
| 6,436,438 B1 | 8/2002 | Momberger et al. | |
| 7,815,934 B2 | 10/2010 | Boehm | |
| 2003/0064099 A1* | 4/2003 | Oshlack et al. | ............... 424/465 |
| 2005/0214372 A1* | 9/2005 | Di Capua et al. | ............. 424/472 |
| 2006/0039981 A1* | 2/2006 | Murpani et al. | ............... 424/487 |
| 2006/0210630 A1 | 9/2006 | Liang et al. | |
| 2007/0092565 A1 | 4/2007 | Aurora et al. | |

(Continued)

FOREIGN PATENT DOCUMENTS

| | | |
|---|---|---|
| EP | 0 344 704 A1 | 12/1989 |
| EP | 0 635 265 | 1/1995 |

(Continued)

OTHER PUBLICATIONS

Zou et al (Journal of Pharmaceutical Sciences, 2008, vol. 97, pp. 263-273).*

(Continued)

*Primary Examiner* — Brian-Yong Kwon
*Assistant Examiner* — Mark V Stevens
(74) *Attorney, Agent, or Firm* — Oliff PLC

(57) ABSTRACT

Granules having a solid core on which an active ingredient is supported, the core being chosen preferably from among insoluble supports, the granules also having, supported on said the core, the following compounds: one or more coloring agents, one or more metallic pigments, one or more gas-releasing compounds, and optionally one or more embittering agents.

10 Claims, No Drawings

(56) References Cited

U.S. PATENT DOCUMENTS

| | | | |
|---|---|---|---|
| 2007/0270491 A1 | 11/2007 | Cook et al. | |
| 2008/0081068 A1* | 4/2008 | Oberegger et al. | 424/465 |
| 2009/0011016 A1* | 1/2009 | Cailly-Dufestel et al. | 424/465 |
| 2009/0175939 A1* | 7/2009 | Bosse et al. | 424/472 |
| 2010/0249045 A1* | 9/2010 | Babul | 514/21.4 |
| 2011/0293729 A1 | 12/2011 | Lebon et al. | |
| 2012/0207843 A1 | 8/2012 | Lebon et al. | |

FOREIGN PATENT DOCUMENTS

| | | | |
|---|---|---|---|
| EP | 1 293 209 A1 | | 3/2003 |
| FR | 2 829 932 A1 | | 3/2003 |
| FR | 2829932 A1 | * | 3/2003 |
| GB | 2 331 702 A | | 6/1999 |
| WO | WO 93/00083 A | | 1/1993 |
| WO | WO 00/66089 A1 | | 11/2000 |
| WO | WO 01/10417 A1 | | 2/2001 |
| WO | WO 01/80822 A2 | | 11/2001 |
| WO | WO 02/085336 A1 | | 10/2002 |
| WO | WO 03/013479 A1 | | 2/2003 |
| WO | WO 03/026621 A2 | | 4/2003 |
| WO | WO 2005/079760 A1 | | 9/2005 |
| WO | WO 2005/101983 A2 | | 11/2005 |

OTHER PUBLICATIONS

Lin et al. (Journal of Microencapsulation, 1999, vol. 16, pp. 639-646).*
PharmaTrans SANAQ (Cellets—Microcrystalline Cellulose Pellets, Jul. 7, 2007).*
Cellets Information Sheet (Aug. 2008, pp. 1-4).*
Feb. 3, 2011 International Search Report issued in International Patent Application No. PCT/FR2010/051697.
Mar. 13, 2012 International Preliminary Report on Patentability issued in International Patent Application No. PCT/FR2010/051697 (with translation).
Mar. 30, 2011 International Search Report issued in International Patent Application No. PCT/FR2010/051691 (with translation).
Rouge et al., "Buoyancy and Drug Release Patterns of Floating Minitablets Containing Piretanide and Atenolol as Model Drugs," *Pharmaceutical Development and Technology*, vol. 3, No. 1, pp. 73-84, 1998.
Elkheshen et al., "In vitro and in vivo Evaluation of Floating Controlled Release Dosage Forms of Verapamil Hydrochloride," *Pharmazeutische Industrie*, vol. 66, No. 11, pp. 1364-1372, 2004.
Sawicki et al., "Compressibility of floating pellets with verapamil hydrochloride coated with dispersion Kollicoat SR 30 D," *European Journal of Pharmaceutics and Biopharmaceutics*, vol. 60, pp. 153-158, 2005.
Sauzet et al., "An innovative floating gastro retentive dosage system: Formulation and in vitro evaluation," *International Journal of Pharmaceutics*, vol. 378, pp. 23-29, 2009.
Goole et al., "Development and evaluation of new multiple-unit levodopa sustained-release floating dosage forms," *International Journal of Pharmaceutics*, vol. 334, pp. 35-41, 2007.
Jan. 15, 2010 International Search Report issued in International Application No. PCT/FR2009/052169 (with English Translation).
PCT/FR2009/052169: Written Opinion of the International Searching Authority (undated) issued in International Application No. PCT/FR2009/052169, 6 pages.
Oct. 26, 2012 Office Action issued in U.S. Appl. No. 13/129,130.

* cited by examiner

PHARMACEUTICAL FORMULATIONS TO PREVENT THE MISUSE OF MEDICINAL DRUGS

The present invention relates to novel pharmaceutical formulations to limit or indeed prevent the misuse of medicinal drugs.

Misuse of medicinal drugs is equivalent to inappropriate use thereof. This phenomenon is a major and constantly increasing public health problem. Misuse arises from the duality of some active ingredients which are both medicinal therapeutic substances and at the same time illegal drugs.

The objectives aimed for when this misuse occurs are of several types, specifically: a search for intellectual or physical performance; pleasure seeking in a party or rave context; addiction problems following initial use relief from physical or psychological symptoms; in some cases chemical control, such as sexual abuse while under the influence of a drug, and also occasionally genuine accidental misuse or improper use of a medicinal drug, for example through a lack of understanding on the part of elderly people.

The consequences of this misuse are many and varied; simple secondary effect, tissue necrosis locally administered misuse, heart disorders; respiratory depression, addiction or even criminal offences, particularly rape.

At present, relatively few means are available and these are basically administrative: inclusion of the substances concerned in lists subject to special legislation, issue by secured prescription and issue in a hospital environment with restricted issue rules. Pharmaceutical companies are also seen to be making efforts to package these products to prevent, in particular, accidental ingestion by children.

Recently, studies have been carried out at the galenic level on the formulations themselves.

For example, in the case of addictive behaviour or when chemical control is sought, the people concerned who seek to use a medicinal drug inappropriately will usually either ingest the medicinal drug directly or try to extract the active ingredient.

The first step therefore is to obtain powder from the medicinal compound by crushing. The active ingredient is then either directly ingested or inhaled and is usually extracted by an aqueous or alcoholic solvent.

International application WO03/013479 thus describes the association of an opium-containing analgesic with its antagonist which significantly blocks the euphoric effect of the opioid analgesic. Both compounds are released at the same time. However, this type of pharmaceutical formulation comprising an opium-containing agonist and its antagonist has drawbacks. In reality, the use of a pharmacologically active antagonist may be the cause of various problems.

Application EP 1 293 209 describes a modified release form using an ion exchange resin which limits extraction by chewing or use by inhalation or injection. However, this type of formulation does not prevent extraction using solvents or crushing.

International application WO2005/079760 describes a multi-particulate formulation using a plastic polymer (Eudragit® NE30D) which, because of its plastic properties and the concomitant use of a plasticizer, makes it difficult to crush said formulation. However, no provision is made with this formulation to prevent extraction by solvent.

At present, sustained release formulations therefore exist which use different galenic ploys to obtain this modified release, but none of the systems described can guard against the illegal extraction of the active ingredient. Such a formulation therefore needs to be developed.

An object of the present invention is therefore to provide pharmaceutical formulations specifically designed to prevent the inappropriate use of medicinal drugs.

An object of the present invention is to provide pharmaceutical formulations to guard against illicit extraction of the active ingredient.

An object of the present invention is to provide medicinal compounds, particularly oral compounds, specially formulated to provide greater security against the problems of inappropriate use of medicinal drugs.

An object of the present invention is to provide pharmaceutical formulations that remedy and add to existing devices in order to reduce and render impossible the inappropriate use of medicinal drugs.

Another object of the present invention is to provide pharmaceutical formulations that give the therapeutic effect sought and that alone.

Another object of the present invention is to provide pharmaceutical formulations of a form and size that allow them to be easily administered and used.

The present invention therefore relates to granules comprising a solid core on which an active ingredient is supported, said core being chosen preferably from among insoluble supports, and more particularly from the group of polyols such as sorbitol, xylitol or maltitol, gums, silicone derivatives, derivatives of calcium or potassium, mineral compounds such as dicalcic phosphates, tricalcic phosphates and calcium carbonates, saccharose, cellulose derivatives, particularly microcrystalline cellulose, ethyl cellulose and hydroxypropyl methyl cellulose, starch and mixtures thereof, said granules also comprising, supported on said solid core, the following compounds:

one or more colouring agents,
one or more metallic pigments,
one or more gas-releasing compounds, and
possibly one or more embittering agents associated with the active ingredient.

The present invention therefore provides pharmaceutical formulations comprising the use of a plurality of galenic ploys to render impossible each of the techniques encountered at the time of inappropriate use. These formulations, based on the above-mentioned granules, are monolithic (tablets) or multi-particulate in form. Said granules according to the invention therefore comprise a plurality of layers of different composition each with a particular function.

The expression "granule" refers to a preparation consisting of solid dry grains, each forming an aggregate of powder particles of sufficient solidity to allow various processing steps.

From a physical point of view, the granules are aggregates of various crystallised or amorphous powder particles.

The granules according to the present invention are intended in particular for oral administration, and more particularly to be swallowed as they are.

The granules according to the present invention have a characteristic core-cortex structure, where the nature of the core is not the same as the compounds forming the cortex.

Accordingly, the granules have a multi-layer structure. The active ingredient is deposited on the core and thus forms a layer or cortex deposited around the core or support.

The core of the granules may also be regarded as a support on which the particles of the active ingredient will be attached.

The core comprises solid particles and the active ingredient supported on said core is also solid.

The present invention is therefore based, on the development of a novel multi particulate oral form.

The granules according to the invention have an active ingredient layer.

Depending on the final pharmacological parameters required, the first layer may be covered by other polymeric layers using different coating polymers together with the various additives currently used such as plasticizers, solubilizers, lubricants, anti-adherents and so on.

The granules according to the invention comprise a solid core preferably chosen from supports insoluble in aqueous or alcoholic solvents. By choosing insoluble supports to form the solid core of the granules according to the invention, complete solubilization of the granule is prevented if it is crushed.

The solid core of the granules may also comprise a mixture of compounds, in particular a mixture of insoluble supports. Thus, a mixture of saccharose and starch or silicone- or calcium-derived mineral compounds may be cited.

The solid core may also comprise soluble supports among which may be cited some solid PEG grades, PEG 4000 or PEG 6000 in particular.

The expression "silicone derivatives" refers to silicone and silicone precipitates obtained from alkali silicates, notably Aerosil®, or alternatively talc, bentonite or kaolin.

The expression "calcium derivatives" refers to crystalline excipients derived from calcium hydroxide, products insoluble in water used in medicine as dilutants or filler agents and also as abrasives.

The expression "potassium derivatives" refers in particular to potassium bicarbonate and potassium chloride.

Of the insoluble supports forming the core of the granules according to the invention, magnesium derivatives, particularly carbonates or oxides, may also be cited.

The granules according to the invention alto comprise one or more colouring agents. The colorants are chosen according to their solubility in solvents. For example, a colorant may be chosen for its solubility in ethanol and another for its solubility in water. These two solvents are in fact the ones generally used to extract or solubilize the active ingredients.

The coloration obtained makes it possible to see malicious additions to a drink, for example for chemical control.

The granules according to the invention also comprise one or more metallic pigments.

The presence of colorants and metallic pigments also makes it possible to see any solubilization after crushing the pharmaceutical form and any subsequent ingestion. Similarly, if chewed, an identical phenomenon is observed.

The colorants and metallic pigments may be placed anywhere in the different layers of the granules according to the invention.

Advantageously, there is an intimate mixture of the colorant or colorants with the active ingredient and a metallic pigment is used in the superficial layer of the compound, in other words the one that can be seen on the surface.

The granules according to the invention also comprise in their structure one or more compounds that release gas when the medicinal form is hydrated. Thus, when the granules are poured into a liquid, the presence of such a compound will cause the granules to rise and fall vertically as carbon dioxide is generated and ejected, with a layer of foam appearing on the surface.

This phenomenon is even more obvious when the drink used is already gaseous, for example soda or cola. In this case, a veritable effervescence is observed in the glass.

The use of these galenic solutions gives the final pharmaceutical form maximum guaranteed security against the inappropriate use of this form.

In a preferred form, the above-mentioned granules also comprise a binder, of which the role is to bind the particles to one another, in other words to ensure perfect cohesion of the granule. Binders therefore ensure good cohesion of the active ingredient and the core of the granules.

Accordingly, binders, like the active ingredient, are deposited around the core of the granules.

Most of the hydrophilic excipients that produce viscous solutions, such as gum arabic and gum tragacanth, methyl cellulose and carboxy methyl cellulose, gelatine, starches, maltodextrins, PEG 4000 and 6000 in alcoholic solution, polyvidone in aqueous or alcoholic solution, as well as solutions of saccharose, glucose or sorbitol may be cited as binders.

Binders for the granules according to the invention are chosen preferably from the group of starch, saccharose, gum arable, polyvinylpyrrolidone (PVP or polyvidone), hydroxypropyl methylcellulose (HPMC), gum lac, hydroxypropyl cellulose (HPC), cellulose, polyols or alginates, polyglycolysed glycerides (Gelucire®) or macrogolglycerides, particularly stearoyl macrogolglycerides and also acrylic derivatives, as well as mixtures thereof.

Among the polyols, mannitol, sorbitol, maltitol or xylitol may be cited in particular.

According to a particular embodiment, the binders are preferably selected from the group of polyvinylpyrrolidone, gum lac, polyols or alginates, polyglycolysed glycerides (Gelucire) or macrogolglycerides, notably stearoyl macrogolglycerides, as well as mixtures thereof.

A binder chosen from the above groups may also be used for particular properties; for example it may be beneficial to use as a binder pH-dependent excipients such as EUDRAGIT® L100 or gum lac. Polyglycolysed glycerides (Gelucire®) may also be preferred far their hydrophobic character.

According to a preferred embodiment, the granules according to the invention also comprise one or more embittering agents.

Preferably, said embittering agent is chosen from the group of denatonium benzoate, extracts of, gentian, quinine, caffeine, brucine, quassin, propylthiouracil (PROP), phenylthiocarbamide (PTC), astringent compounds such as tannins, grapefruit flavour and bitter cocoa flavour.

The presence of said embittering agent (or embittering promoter) such as Bitrex® (denatonium benzoate) in intimate mixture with the active ingredient makes absorption by accidental chewing or even after extraction and/or solubilization difficult if not impossible. Said embittering agent in this case is solubilized at the same time as the active ingredient, as differential separation is very difficult.

The use of this type of embittering compound gives a warning of deliberate or underhand administration in the form of "cocktails" in water and alcohol mixtures, such as ice cubes and vodka.

Among the gas-releasing compounds present in the granules according to the invention, compounds chosen from the group of carbonates and bicarbonates in particular may be cited.

More particularly, these compounds are chosen from the group of sodium bicarbonate, sodium carbonate, sodium glycine carbonate, potassium bicarbonate, magnesium carbonate and calcium carbonate.

Among the colouring agents for the granules according to the invention may be cited in particular colouring agents that are soluble in aqueous solvents and colouring agents that are soluble in alcoholic solvents.

Among the colouring agents that are soluble in ethanol may be cited in particular the following: neutral red, brilliant blue FDC, etc.

From among colouring agents soluble in water, conventional food colourings are used. The colourings used in the context of the present invention are in particular those listed in Directive 95/45/EC of 26 Jul. 1995 concerning colourings for use in foodstuffs, amended by Directive 2006/33/EC of 20 Mar. 2006. Accordingly, colourings E100 to E180 in particular may be cited.

Colouring E131 (patent blue) may also be cited which is soluble in both water and ethanol.

According, to a particularly preferred embodiment, the metallic pigments used in the granules according to the invention are titanium dioxide-based pigments present on the surface of said granule.

The use of these titanium-based pigments, such as CANDURIN®, proves very beneficial because of the metallic glint they produce, even in very dark-coloured drinks such as Coca-Cola®.

The coated granules comprise grains coated with one or more layers of mixtures of various excipients.

The preferred coated granules according to the present invention therefore comprise an additional layer consisting of the coating agent.

The granules according to the invention may also comprise a coating consisting of a coating agent selected from the group of wax derivatives, plasticizers (film-forming agents), gum lac, polyvinylpyrrolidone, glycol polyethylene, cellulose derivatives such as HPMC or HPC, saccharose, alginates, glycerides of fatty acids and methacrylic polymers.

The expression "wax derivatives" refers to natural or synthetic products consisting of esters of fatty acids and alcohols, normally solid at room temperature and used for different purposes in medicinal preparations.

The granules according to the invention may also be coated by a film to which one or more excipients such as lubricants, colours, sweeteners, plasticizers or anti-adherent agents are added.

The granules according to the invention may also comprise an enteric coating, consisting in particular of methacrylic polymers, notably Eudragit® L, gum lac or HPMCP (hydroxypropyl methylcellulose phthalate-hypromellose phthalate).

Granules of this type are therefore gastro-resistant.

The presence of this enteric coating may affect the bioavailability of the active ingredient, in particular by preventing degradation thereof in an acid environment.

The granules according to the invention may also comprise a sustained release coating.

Granules of this type modify or delay the release of the active ingredients (modified-release granules).

This type of coating is obtained with coating agents comprising in particular Eudragit® S100 acrylate and methacrylate copolymers, gum lac, cellulose derivatives, particularly ethyl cellulose, and acrylic derivatives.

The presence of this modified-release coating affects in particular the apparent half-life of the active ingredient.

The granules according to the invention may alto comprise a lubricant and/or flavour and/or sweetener.

Among the lubricants used in the context of the present invention may be cited in particular talc, magnesium stearate, silicone derivatives, particularly Aerosil® or waxes.

Among the flavours used in the context of the present invention may be cited the flavours traditionally used in food additives.

The sweeteners used in the context of the present invention are in particular those listed in Directive 94/35/EC of 30 Jun. 1994 on sweeteners; for use in foodstuffs (amended by Directive 2006/25/EC of 5 Jul. 2006). Thus, E951 aspartame, E420 sorbitol, E421 mannitol, E950 acesulfame K, E954 saccharin, stevia or thaumatine in particular may be cited.

The granules according to the invention may comprise any active ingredient used in therapeutic pharmacy and combinations thereof. Among the preferred active ingredients may be cited antalgics and analgesics.

Analgesics are painkillers. Among the analgesic categories may be cited in particular morphine-based central analgesics (morphine derivatives), non-morphine-based central analgesics, peripheral analgesics and others such as benzodiazepines.

Preferably, the active ingredients of the granules according to the invention are chosen from the group of morphine sulphate, oxycodone, gamma-hydroxybutyric acid or one of its salts, buprenorphine, modafinil, dextropropoxyphene, methadone, tramadol, nalbuphine, tetrahydrocannabinol and benzodiazepines.

According to a preferred embodiment, the granules according to the present invention do not comprise an antagonist of the active ingredient. The granules according to the present invention therefore have the advantage of not containing an agent that modifies the therapeutic action of the active ingredient.

Said granules therefore provide the therapeutic effect sought and that alone, in other words other active compounds, such as an antagonist of the active ingredient, are not used.

According to another preferred embodiment, the granules according to the present invention do not comprise an ion exchange resin.

Preferably, the granules according to the invention comprise from 0.5% to 60% by weight of active ingredient in relation to the total weight of the granule.

Preferably, the granules according to the invention comprise from 0.2% to 4% by weight of colouring agent in relation to the total weight of the granule.

Preferably, the granules according to the invention comprise from 0.1% to 5% by weight of metallic pigments in relation to the total weight of the granule.

Preferably, the granules according to the invention comprise from 5% to 20% by weight of gas-releasing compounds in relation to the total weight of the granule.

Preferably, in the granules according to the invention, the solid core represents from 10% to 85% by weight in relation to the total weight of the granule.

The present invention also relates to a pharmaceutical compound comprising granules as defined above.

The present invention also relates to a process of preparing a granule as defined above, characterised in that it comprises a step of applying the active ingredient to the insoluble support by powdering.

According to a preferred embodiment of the process according to the invention, the active ingredient is mixed with the colouring agents, the metallic pigments and the gas-releasing compounds before the step of applying to the insoluble support by powdering.

The process according to the invention may also comprise, after the powdering step, a granule coating step, in particular by depositing the coating agent in the form of a film on the granule by film-coating, followed if appropriate by a step of mixing with a lubricant and/or flavour and/or sweetener and/or colour or metallic pigment.

The structure of the granules according to the invention is linked to the use of this particular process which produces granules with a core-cortex structure.

When carrying out comparative granule preparation tests by a direct granulation process with different excipients normally used for granulation, it was observed that the results obtained for the granule itself are satisfactory as regards appearance, friability and dissolution. However, the granules obtained by this type of process, a very high specific surface area which requires large amounts of coating polymers according to the techniques in conventional use.

The granules according to the invention are therefore characterised in that they have a reduced specific surface area. Moreover, they are relatively smooth in appearance and have a fairly regular form.

The above-mentioned powdering step of the process for preparing the granules according to the invention may also comprise a step in which an alcoholic, hydroalcoholic or aqueous binder solution is sprayed.

This spraying step and the powdering step are preferably carried out simultaneously or alternately.

Preferably, the above-mentioned powdering step is carried out at the same time as step in which a binder is sprayed in solution form.

The combination of these steps ensures good cohesion of the active ingredient on the core of the granules.

An advantageous way of carrying out the process according to the invention therefore involves applying the active ingredient in powder form to the above-mentioned particulate support for granule core), by alternating the sequences of spraying the binder in solution form.

The process according to the invention may also comprise, after the powdering step, one or more steps in which the granule is coated, in particular by depositing the coating agent or agents in the form of a film on the granule by film-coating.

For coating, the low specific surface area of the granules according to the invention therefore reduces the amount of coating agent used and thus reduces dilution of the active ingredient in said coated granules.

A preferred embodiment of the process according to the invention is a process comprising, after the coating stop, a step of mixing with a lubricant and/or flavour and/or sweetener, which may themselves be prepared in granule form in order eventually to be mixed with the active granules.

However, the lubricants, flavours and sweeteners may also be added before the above-mentioned powdering step.

EXAMPLES

The examples below relate to particular examples of pharmaceutical formulations according to the invention based on the above-mentioned granules.

Example 1

Morphine Sulphate-Based Tablets

| 60 mg SR morphine sulphate tablets | mg | % |
|---|---|---|
| Dry base materials | | |
| Morphine sulphate | 60.000 | 40.00 |
| Bitrex ® | 0.200 | 0.133 |
| Sodium bicarbonate | 15.000 | 10.00 |
| HPMC 100000 SR | 65.000 | 43.33 |
| Aerosil ® 972 | 1.000 | 0.67 |
| Candurin ® blue Amber | 0.500 | 0.33 |
| Patent blue | 0.500 | 0.33 |
| SEPIFILM ® LP014 | 4.500 | 3.00 |

-continued

| 60 mg SR morphine sulphate tablets | mg | % |
|---|---|---|
| Talc | 3.000 | 2.00 |
| Magnesium stearate | 0.300 | 0.20 |
| Solvents | | |
| 96° alcohol | QS | |
| Purified water | QS | |
| Theoretical mass | QS | |
| Dry theoretical mass | 150.000 | 100.00 |
| Theoretical content (mg/g) | 400.00 | |

The above-mentioned tablets were obtained using the following operating process:

An initial mixture (mixture 1) was prepared with denatonium benzoate (Bitrex®), silicone (Aerosil®972), talc, sodium bicarbonate (a gas-releasing compound) and patent blue (colour). These compounds were mixed together in a Turbula® mixer for ten minutes.

A second mixture (mixture 2) was also prepared by introducing the active ingredient after micronization into the mixer. All of this was then mixed with the HPMC for twenty minutes.

Next, mixture 1 was introduced into mixture 2 for a further twenty minutes.

The resulting mixture was then used in direct compression in a Korsch 3 punch machine to produce tablets.

The tablets obtained were then film-coated with a coating suspension comprising SEPIFILM® LP, colour and magnesium stearate.

Example 2

Oxycodone-Based Granules

| 2 mg SR oxycodone granules | mg | % |
|---|---|---|
| Dry base materials | | |
| Oxycodone | 2.000 | 0.67 |
| Mannitol granules | 131.44 | 43.81 |
| Microcrystalline cellulose | 100.00 | 33.33 |
| Bitrex ® | 0.100 | 0.03 |
| Sodium glycine carbonate (SGC) | 15.000 | 5.00 |
| Povidone K30 | 9.000 | 3 |
| Mannitol 60 | 30.000 | 10.00 |
| Pigments | 0.500 | 0.17 |
| Colour | 0.500 | 0.17 |
| Ethyl cellulose | 9.000 | 3.00 |
| Hydrogenated ricin oil | 2.160 | 0.72 |
| Talc | 0.300 | 0.10 |
| Solvents | | |
| 96° alcohol | Qs | |
| Purified water | Qs | |
| Theoretical mass | Qs | |
| Dry theoretical mass | 300.000 | 100.00 |
| Theoretical content (mg/g) | 6.67 | |

The above-mentioned granules were obtained using the following operating process:

First, an active suspension was prepared by preparing an aqueous suspension containing the active ingredient (oxycodone), the binder (PVP), the pigment and the embittering agent (Bitrex®).

Said suspension was then sprayed on the support (mannitol granules in a fluidised air bed) and the granules were then dried in the air bed.

An initial mixture (mixture 1) was prepared from granules of mannitol, microcrystalline cellulose and glycine carbonate (a gas-releasing compound).

A second mixture (mixture 2) was also prepared from the above-mentioned granules obtained from the active ingredient. These granules were dried then placed in the mixer before the introduction of colours and lubricants.

Finally, mixtures 1 and 2 were mixed and measured.

Example 3

Buprenorphine-Based Capsules

| 8 mg SR buprenorphine capsules | mg | % |
|---|---|---|
| Dry base materials | | |
| Buprenorphine | 8.000 | 2.00 |
| Neutral sugar starch | 289.61 | 72.40 |
| Bitrex ® | 0.200 | 0.05 |
| Sodium bicarbonate | 26.250 | 6.56 |
| Ethyl cellulose | 9.000 | 2.25 |
| Mannitol 60 | 30.000 | 7.50 |
| Pigments | 0.500 | 0.13 |
| Colour | 0.500 | 0.13 |
| Aquacoat EC30D ® | 28.500 | 7.13 |
| Plasticizers | 6.840 | 1.71 |
| Talc | 0.600 | 0.15 |
| Solvents | | |
| 96° alcohol | Qs | |
| Purified water | Qs | |
| Theoretical mass | Qs | |
| Dry theoretical mass | 400.000 | 100.00 |
| Theoretical content (mg/g) | 20.00 | |

The above-mentioned capsules were obtained using the following operating process:

Neutral supports (sugar/starch) were placed in a conventional turbine and an aqueous suspension was prepared containing the active ingredient (buprenorphine), the binder and the embittering agent. Sodium bicarbonate (a gas-releasing compound) was then deposited by powdering on the sugar and starch supports alternating the powdering and suspension spraying phases.

The granules obtained were then turbine dried.

A coating was then applied with an aqueous suspension of ethyl cellulose comprising the plasticizer, a colour and talc.

The granules were then subjected to a further drying stet) to harden the film.

Finally, the granules were then divided into capsules.

Example 4

Modafinil-Based Capsules

| 200 mg IR modafinil capsules | mg | % |
|---|---|---|
| Dry base materials | | |
| modafinil | 200.000 | 40.00 |
| Neutral cellulose | 187.86 | 37.57 |
| Bitrex ® | 0.200 | 0.04 |
| Sodium carbonate | 40.000 | 8.00 |
| Povidone | 30.000 | 6.50 |
| Pigments | 0.500 | 0.10 |
| Aerosil R972 ® | 5.000 | 1 |
| Colour | 0.500 | 0.10 |

| 200 mg IR modafinil capsules | mg | % |
|---|---|---|
| Methacrylic polymer | 28.500 | 5.70 |
| Plasticizer | 6.840 | 1.37 |
| Talc | 0.600 | 0.12 |
| Solvents | | |
| 96° alcohol | Qs | |
| Purified water | Qs | |
| Theoretical mass | Qs | |
| Dry theoretical mass | 500.000 | 100.00 |
| Theoretical content (mg/g) | 400.00 | |

The above-mentioned capsules were obtained using the following operating process:

The cellulose supports were placed in a conventional turbine.

After micronization, the active ingredient was mixed with sodium carbonate and this mixture was then applied by powdering on supports rotating in the turbine.

A solution was then prepared with the Bitrex® and pigments by incorporating them in, the alcoholic PVP binder solution. This solution was then sprayed on the supports alternating with the powdering phases.

The granules obtained were then dried to eliminate the solvents used in the active ingredient powdering step.

The coating suspension was prepared by preparing a suspension of methacrylic polymers to which the plasticizer, lubricants and colour were added. This suspension was then subjected to agitation then sprayed on the granules which had previously been obtained.

The coated granules obtained in this way were then dried once more and divided into capsules.

Example 5

GHB (Gamma-Hydroxybutyric Acid) Granules

| GHB ampoule | g (amount per ampoule) | % |
|---|---|---|
| Dry base materials | | |
| GHB | 1.75 | 57.48 |
| Sugar spheres | 0.61 | 11.48 |
| Sodium bicarbonate | 0.26 | 8.52 |
| Shellac/gum lac (E 904) | 0.20 | 6.56 |
| Neusilin UFL2 ® | 0.16 | 5.25 |
| Sepifilm ® LP014 | 0.02 | 0.66 |
| Pharmacoat ® 603 | 0.03 | 0.98 |
| Talc | 0.02 | 0.66 |
| Embittering agent Bitrex ® | 0.2 | 6.56 |
| Colour | 0.06 | 1.97 |
| Solvents | | |
| 96° alcohol | Qs | |
| Purified water | Qs | |
| Theoretical mass | Qs | |
| Dry theoretical mass | 3.05 | 100.00 |

The microgranules of example 5 were prepared by loading the active ingredient (GHB) on sugar spheres.

The active ingredient GHB was mixed with sodium bicarbonate and the compound Neusilin® (magnesium aluminometasilicate). The mixture thus obtained was crushed.

At the same time, a solution was prepared with shellac resin and ethanol which was then added to the above-mentioned mixture. The sugar spheres were then also added.

All of this was then dried and covered with a coating obtained from a mixture of the coating agents Sepifilm® and Pharmacoat® solubilized in water and ethanol.

All of this was then dried once again and covered with a second coating obtained from a mixture of shellac resin and talc solubilized in water and ethanol.

Finally, the granules thus obtained were dried before adding talc as a lubricant.

The invention claimed is:

1. A granule having a core-shell structure, comprising:
a solid core of a material that is at least one selected from the group consisting of sorbitol, xylitol, maltitol, mannitol, gums, silica, silicone compounds, dicalcic phosphates, tricalcic phosphates, potassium chloride, crystalline excipients derived from calcium hydroxide, calcium carbonates, magnesium carbonates, saccharose, cellulose compounds, starch and mixtures thereof, the core representing from 10% to 85% of a total weight of the granule; and
a shell surrounding the core, the shell being of a different material than the material of the core and comprising:
an active ingredient in an amount of from 0.5% to 60% by weight in relation to the total weight of the granule, the active ingredient being selected from the group consisting of morphine sulphate, oxycodone, gamma-hydroxybutyric acid or one of its salts, buprenorphine, modafinil, dextropropoxyphene, methadone, tramadol, nalbuphine, tetrahydrocannabinol and benzodiazepines,
one or more colouring agents in an amount of from 0.2% to 4% by weight in relation to the total weight of the granule, the colouring agents being soluble in aqueous solvents,
one or more metallic pigments in an amount of from 0.1% to 5% by weight in relation to a total weight of the granule, the metallic pigments being insoluble in aqueous solvents,
one or more gas-releasing compounds in an amount of from 5% to 20% by weight in relation to a total weight of the granule, the gas-releasing compounds being selected from the group consisting of sodium carbonates, sodium bicarbonates, sodium glycine carbonates and potassium bicarbonates,
one or more embittering agents in intimate mixture with the active ingredient, the embittering agents being selected from the group consisting of denatonium benzoate, brucine and phenylthiocarbamide (PTC),
wherein
when the granule comes in contact with a liquid, the gas-releasing compound causes the granule to rise and fall vertically as carbon dioxide is generated and a layer of foam to appear on a surface of the liquid,
the granule does not contain an antagonist of the active ingredient, and
the material of the solid core is insoluble in alcoholic solvents.

2. The granule according to claim 1, in which the metallic pigments in the shell are titanium dioxide-based pigments, and are contained in the shell so as to be present on a surface of said granule.

3. A pharmaceutical composition comprising the granules according to claim 1.

4. A process of preparing the granule according to claim 1, comprising:
applying the active ingredient in solid form as the shell surrounding the solid core by powdering.

5. The process according to claim 4, further comprising:
mixing the active ingredient with the colouring agents, metallic pigments and gas-releasing compounds before applying the active ingredient as the shell surrounding the solid core by powdering.

6. The granule according to claim 1, wherein the material of the core is cellulose compounds, the cellulose compounds being selected from the group consisting of microcrystalline cellulose, ethyl cellulose and hydroxypropyl methyl cellulose.

7. The granule according to claim 1, wherein the shell further comprises one or more astringent compounds selected from the group consisting of tannins, grapefruit flavor and bitter cocoa flavor.

8. The granule according to claim 1, wherein the embittering agent is denatonium benzoate.

9. The granule according to claim 1, wherein the active ingredient in the shell layer is cohesively bound to the solid core with a binder that is deposited around the solid core.

10. The granule according to claim 1, wherein the shell surrounding the core further comprises at least one colouring agent soluble in ethanol, and the colouring agent is in intimate mixture with the active ingredient.

* * * * *